United States Patent
Yao et al.

(10) Patent No.: US 11,237,152 B2
(45) Date of Patent: Feb. 1, 2022

(54) WIRELESS TRANSMITTER ADAPTERS FOR BATTERY-OPERATED BIOSENSOR METERS AND METHODS OF PROVIDING SAME

(71) Applicant: ASCENSIA DIABETES CARE HOLDINGS AG, Basel (CH)

(72) Inventors: Raymond L. Yao, Ossining, NY (US); Lauren N. Bock, Elmsford, NY (US); Igor Y. Gofman, Croton-on-Hudson, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 399 days.

(21) Appl. No.: 15/303,218

(22) PCT Filed: Apr. 9, 2015

(86) PCT No.: PCT/US2015/025213
§ 371 (c)(1),
(2) Date: Oct. 10, 2016

(87) PCT Pub. No.: WO2015/157582
PCT Pub. Date: Oct. 15, 2015

(65) Prior Publication Data
US 2017/0030889 A1 Feb. 2, 2017

Related U.S. Application Data

(60) Provisional application No. 61/978,595, filed on Apr. 11, 2014.

(51) Int. Cl.
*G01N 33/487* (2006.01)
*G08C 17/02* (2006.01)
(Continued)

(52) U.S. Cl.
CPC ....... *G01N 33/48792* (2013.01); *G08C 17/02* (2013.01); *A61B 5/0002* (2013.01); *A61B 5/14532* (2013.01); *A61B 2560/045* (2013.01)

(58) Field of Classification Search
CPC ..... A61B 5/0002; A61B 5/0004; A61B 5/145; A61B 5/14507; A61B 5/14532;
(Continued)

(56) References Cited

U.S. PATENT DOCUMENTS

| 5,575,403 A | 11/1996 | Charlton et al. |
| 6,540,672 B1 | 4/2003 | Simonsen |

(Continued)

FOREIGN PATENT DOCUMENTS

| CN | 1921529 A | 2/2007 |
| CN | 101461969 A | 6/2009 |

(Continued)

OTHER PUBLICATIONS

International Preliminary report on Patentability of related International Application No. PCT/US2014/062404 dated Jan. 19, 2017.
(Continued)

*Primary Examiner* — Franklin D Balseca
(74) *Attorney, Agent, or Firm* — Dugan & Dugan, PC

(57) ABSTRACT

A wireless transmitter adapter (206) can provide wireless data transmission capability to a battery-operated biosensor meter (100), such as a blood glucose meter, originally configured for hardwired data downloads. In some embodiments, the wireless transmitter adapter (206) can be configured to replace a bio-sensor meter's battery cover (106). The wireless transmitter adapter (206) can include wireless transmitter circuitry (700), a connector (218) configured to be received in a biosensor meter's communications port (112) to electrically couple to the meter's processor circuitry (107), and one or more electrical contacts (625a, 625b)
(Continued)

configured to electrically couple to the biosensor meter's one or more batteries (102a, 102b) to power the wireless transmitter circuitry (700). In other embodiments, the wireless transmitter adapter (206) can be configured to surround at least a portion of a biosensor meter (100) and to include its own battery compartment (804) to separately provide power to the wireless transmitter circuitry (700). Methods of providing a wireless transmitter adapter (206) for battery-operated biosensor meters (100) are also provided, as are numerous other aspects.

9 Claims, 8 Drawing Sheets

(51) Int. Cl.
*A61B 5/00* (2006.01)
*A61B 5/145* (2006.01)

(58) Field of Classification Search
CPC ....... A61B 5/14546; A61B 5/15; A61B 5/157; A61B 2560/0443; A61B 2560/045; G06F 19/3418; G06F 19/34; A61M 2230/20; A61M 2230/201; C12Q 1/54; G01N 33/48792; G08C 17/02
See application file for complete search history.

(56) References Cited

U.S. PATENT DOCUMENTS

| | | |
|---|---|---|
| 6,569,094 B2 | 5/2003 | Suzuki et al. |
| 6,604,050 B2 | 8/2003 | Trippel et al. |
| 6,607,484 B2 | 8/2003 | Suzuki et al. |
| 6,790,178 B1 | 9/2004 | Mault et al. |
| 6,802,812 B1 | 10/2004 | Walker |
| 6,819,013 B2 | 11/2004 | Kelly et al. |
| 6,870,475 B2 | 3/2005 | Fitch et al. |
| 7,286,894 B1 | 10/2007 | Grant et al. |
| 7,316,648 B2 | 1/2008 | Kelly et al. |
| 7,549,961 B1 | 6/2009 | Hwang |
| 7,779,183 B2 | 8/2010 | Koehler et al. |
| 8,131,564 B2 | 3/2012 | Dicks |
| 8,208,973 B2 | 6/2012 | Mehta |
| 8,462,231 B2 * | 6/2013 | Nusbaum ............... H04N 5/772 348/231.2 |
| 8,483,974 B2 * | 7/2013 | Connolly ............. A61B 5/0002 702/32 |
| 8,579,813 B2 | 11/2013 | Causey et al. |
| 8,682,598 B2 | 3/2014 | Connolly et al. |
| 8,755,053 B2 | 6/2014 | Fright |
| 8,758,245 B2 | 6/2014 | Ray et al. |
| 8,895,316 B2 | 11/2014 | Batman et al. |
| 8,954,007 B2 | 2/2015 | Hillyard |
| 9,179,844 B2 | 11/2015 | Fright |
| 9,462,623 B2 | 10/2016 | Jakusovszky |
| 9,696,980 B2 | 7/2017 | Dicks |
| 9,750,896 B2 | 9/2017 | Kamen |
| 9,861,285 B2 | 1/2018 | Fright |
| 10,177,599 B2 * | 1/2019 | Abe .................... H02J 50/90 |
| 2001/0038343 A1 * | 11/2001 | Meyer ................ G01D 4/004 340/870.02 |
| 2006/0009697 A1 | 1/2006 | Banet et al. |
| 2006/0106433 A1 | 5/2006 | Mazar et al. |
| 2006/0273930 A1 | 12/2006 | Godden |
| 2007/0003061 A1 | 1/2007 | Jung et al. |
| 2007/0027388 A1 | 2/2007 | Chou |
| 2007/0171088 A1 | 7/2007 | Sato |
| 2007/0181425 A1 | 8/2007 | Kim |
| 2007/0254709 A1 | 11/2007 | Higgins |
| 2007/0293910 A1 | 12/2007 | Strother et al. |
| 2007/0299480 A1 | 12/2007 | Hill |
| 2008/0092638 A1 | 4/2008 | Brennenman et al. |
| 2008/0109302 A1 | 5/2008 | Salokannel et al. |
| 2009/0069642 A1 | 3/2009 | Gao et al. |
| 2009/0091626 A1 * | 4/2009 | Kaplan ............... H04N 5/2252 348/207.1 |
| 2009/0116479 A1 | 5/2009 | Choi |
| 2009/0163793 A1 | 6/2009 | Koehler |
| 2009/0198141 A1 * | 8/2009 | Hollinger ........... G06F 19/3418 600/490 |
| 2009/0213213 A1 | 8/2009 | Fright |
| 2009/0243791 A1 * | 10/2009 | Partin .................... G08C 17/00 340/5.2 |
| 2010/0000862 A1 | 1/2010 | Rao |
| 2010/0055981 A1 * | 3/2010 | Yang .................... H01R 13/60 439/620.21 |
| 2010/0111066 A1 | 5/2010 | Mehta |
| 2010/0113897 A1 | 5/2010 | Brennenman et al. |
| 2010/0165795 A1 | 7/2010 | Elder |
| 2010/0228111 A1 * | 9/2010 | Friman ............... A61B 5/14532 600/365 |
| 2010/0331645 A1 | 12/2010 | Simpson |
| 2011/0066044 A1 | 3/2011 | Moon |
| 2011/0117841 A1 | 5/2011 | Thorn |
| 2011/0165865 A1 | 7/2011 | Gao et al. |
| 2011/0256024 A1 * | 10/2011 | Cole ................... A61B 5/0022 422/68.1 |
| 2011/0319813 A1 | 12/2011 | Kamen |
| 2012/0019379 A1 | 1/2012 | Ben Ayed |
| 2012/0123227 A1 | 5/2012 | Sun et al. |
| 2012/0149245 A1 | 6/2012 | Ralston et al. |
| 2012/0150556 A1 | 6/2012 | Galasso |
| 2012/0190299 A1 | 7/2012 | Takatsuka et al. |
| 2012/0238851 A1 | 9/2012 | Kamen |
| 2013/0190674 A1 | 7/2013 | Case |
| 2014/0094054 A1 * | 4/2014 | Dentzel ................ H01R 13/72 439/501 |
| 2014/0149742 A1 | 5/2014 | Yau |
| 2014/0266607 A1 | 9/2014 | Olodort |
| 2014/0324445 A1 | 10/2014 | Carlsgaard |
| 2014/0364056 A1 | 12/2014 | Belk |
| 2014/0380218 A1 | 12/2014 | Refvik |
| 2015/0123810 A1 | 5/2015 | Hernandez-Rosas |
| 2016/0337448 A1 | 11/2016 | Gofman et al. |
| 2017/0030889 A1 | 2/2017 | Yao et al. |
| 2017/0038847 A1 | 2/2017 | Schorsch |
| 2017/0201931 A1 | 7/2017 | Swanzey et al. |
| 2017/0208425 A1 | 7/2017 | Fu et al. |
| 2017/0214780 A1 | 7/2017 | Gofman et al. |
| 2017/0344718 A1 | 11/2017 | Chen |

FOREIGN PATENT DOCUMENTS

| | | |
|---|---|---|
| CN | 201491011 U | 5/2010 |
| CN | 202075262 U | 12/2011 |
| CN | 102565413 A | 7/2012 |
| CN | 202838653 U | 3/2013 |
| CN | 205006870 U | 2/2016 |
| EP | 2352305 | 8/2011 |
| EP | 2741 528 | 6/2014 |
| EP | 2887753 | 6/2015 |
| JP | 2007-111514 | 5/2007 |
| JP | 2007-228554 | 9/2007 |
| JP | 2007-243372 | 9/2007 |
| JP | 2010-124286 | 6/2010 |
| JP | 2011-511335 | 4/2011 |
| JP | 2012-157006 | 8/2012 |
| JP | 2013-201516 A | 10/2013 |
| JP | 2014-068076 | 4/2014 |
| TW | 201322167 A | 6/2013 |
| WO | WO0152727 | 7/2001 |
| WO | WO 2008/153825 | 12/2008 |
| WO | WO 2009/006486 | 1/2009 |
| WO | WO2009/074887 | 6/2009 |
| WO | WO2013066362 | 5/2013 |
| WO | WO 2014/146021 | 9/2014 |
| WO | WO 2015/157582 | 10/2015 |
| WO | WO 2016/007186 | 1/2016 |
| WO | WO 2016/007187 | 1/2016 |

(56) References Cited

FOREIGN PATENT DOCUMENTS

| WO | WO 2016/007188 | 1/2016 |
|---|---|---|
| WO | WO 2016/174206 | 11/2016 |

OTHER PUBLICATIONS

International Preliminary Report on Patentability of related International Application No. PCT/US2014/062472 dated Jan. 19, 2017.
International Preliminary Report on Patentability of related International Application No. PCT/US2014/062433 dated Jan. 19, 2017.
International Search Report and Written Opinion of related International Application No. PCT/US14/69628 dated Mar. 11, 2015.
International Search report of related International Application No. PCT/US2014/062404 dated Mar. 5, 2015.
International Search Report and Written Opinion of related International Application No. PCT/US2014/062433 dated Mar. 23, 2015.
Mare, Shrirang, et al. "ZEBRA: Zero-Effort Bilateral Recurring Authentication", 2014 IEEE Symposium on Security and Privacy, IEEE, May 18, 2014, pp. 705-720.
Mayrhofer, R., et al., "Shake Well before Use: Intuitive and Securing Pairing of Mobile Devices", IEEE Transactions on Mobile Computing, IEEE Service Center, Los Alamitos, CA, US, vol. 8, No. 6, Jun. 1, 2009, pp. 792-806.
International Search Report and Written Opinion of related International Application No. PCT/US2014/062472 dated Mar. 23, 2015.
International Search Report and Written Opinion of related International Application No. PCT/US2015/025213 dated Jun. 15, 2015.
International Preliminary Report on Patentability of related International Application No. PCT/US14/69628 dated Jul. 21, 2016.
International Preliminary Report on Patentability of related International Application No. PCT/US2015/025213 dated Oct. 20, 2016.
International Search Report and Written Opinion of related International Application No. PCT/EP2016/059616 dated Jun. 2, 2016.
International Preliminary Report on Patentability of related International Application No. PCT/EP2016/059616 dated Nov. 9, 2017.
Chinese Search report of related Chinese Application No. 201580031100.3 dated Jul. 19, 2018.
Taiwan Search report of related Taiwan Application No. 103143687 dated Sep. 17, 2018.
Chinese Search report of related Chinese Application No. 201480076629.2 dated Dec. 11, 2018.

* cited by examiner

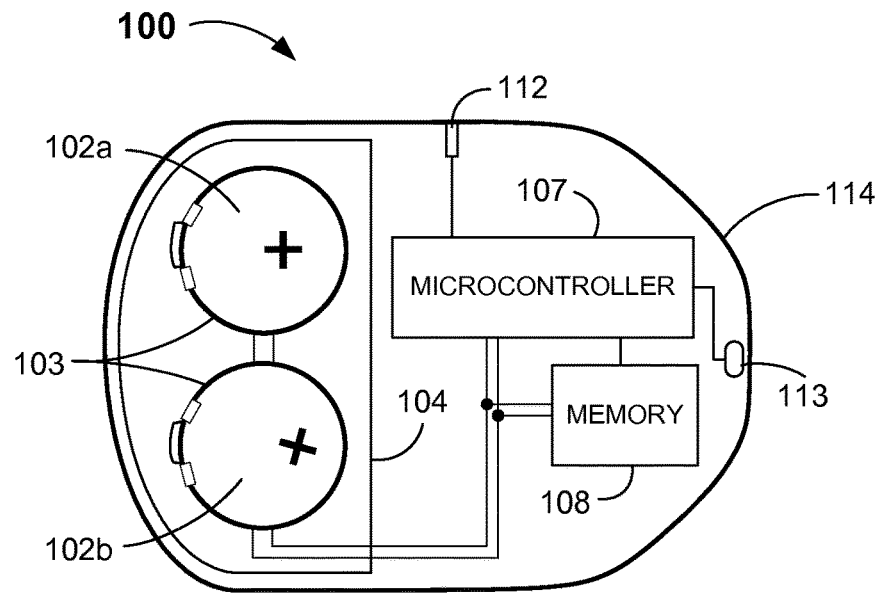
FIG. 1A
PRIOR ART
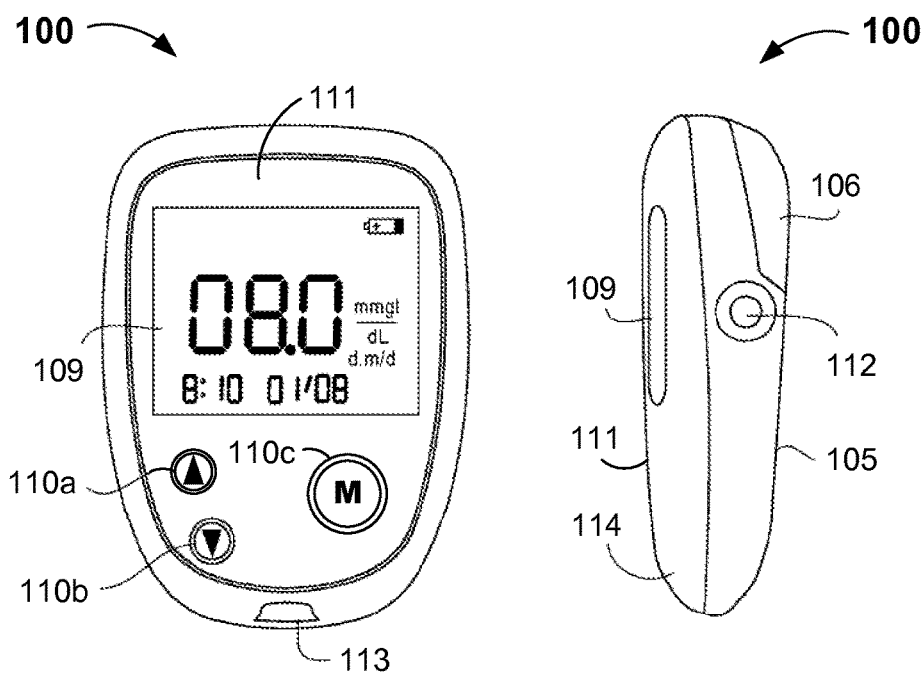
FIG. 1B
PRIOR ART
FIG. 1C
PRIOR ART

WIRELESS TRANSMITTER ADAPTERS FOR BATTERY-OPERATED BIOSENSOR METERS AND METHODS OF PROVIDING SAME

RELATED APPLICATION

The present application claims priority to U.S. Provisional Patent Application No. 61/978,595, Filed Apr. 11, 2014 and entitled "WIRELESS TRANSMITTER ADAPTERS FOR BATTERY-OPERATED BIOSENSOR METERS AND METHODS OF PROVIDING SAME," which is hereby incorporated herein by reference for all purposes.

FIELD

The invention relates generally to biosensor meters, such as, e.g., blood glucose meters, and more particularly to wireless battery-operated biosensor meters.

BACKGROUND

Biosensor meters, such as blood glucose meters, can be used to detect and/or monitor an amount or concentration of an analyte such as glucose in a fluid sample such as blood. Users of biosensor meters may need to test a fluid sample several times a day while at home, work, school, and/or various other places. Battery-operated biosensor meters allow users to carry the biosensor meters with them and to use the meters almost anywhere. Many known battery-operated biosensor meters rely on a proprietary cable, such as, e.g., a USB (universal serial bus) or RS232 cable, for connecting the biosensor meter to a computer or like device for downloading measurement data from the biosensor meter. Such cables, however, are easily misplaced, forgotten, or lost, and thus may delay or prevent a user from downloading measurement data from the biosensor meter. A need therefore exists to provide known battery-operated biosensor meters with an alternative to hardwired downloading of measurement data.

SUMMARY

According to one aspect, a wireless transmitter adapter configured for a biosensor meter is provided. The wireless adapter comprises a body configured to be disposed about and conform to at least a portion of the biosensor meter; a connector configured to be received in a communications port of the biosensor meter to electrically couple to circuitry in the biosensor meter via the communications port; and wireless transmitter circuitry housed within the body, the wireless transmitter circuitry electrically coupled to the connector and configured to wirelessly transmit data from the biosensor meter.

According to another aspect, a biosensor meter is provided. The biosensor meter comprises a battery holder configured to receive one or more batteries; a microcontroller configured to be powered by the one or more batteries and to determine a property of an analyte in a fluid; a memory configured to be powered by the one or more batteries and coupled to the microcontroller to store data including a determined property of an analyte in a fluid; a housing configured to house the battery holder, the microcontroller, and the memory; a communications port disposed in the housing and configured to electrically couple a cable received in the communications port to the microcontroller; and a wireless transmitter adapter comprising a body disposed about at least a portion of the housing; a connector configured to be received in the communications port to electrically couple to the microcontroller; and wireless transmitter circuitry located within the body and electrically coupled to the connector to wirelessly transmit data from the biosensor meter.

According to a further aspect, a method of providing a wireless transmitter adapter configured for a biosensor meter capable of hardwired downloading of data is provided. The method comprises configuring a body of the wireless transmitter adapter to be disposed about and conform to at least a portion of the biosensor meter; providing a connector configured to be received in a communications port of the biosensor meter to electrically couple to circuitry of the biosensor meter via the cable port; and providing wireless transmitter circuitry within the body, the wireless transmitter circuitry electrically coupled to the connector and configured to wirelessly transmit data from the biosensor meter.

Still other aspects, features, and advantages of the invention may be readily apparent from the following detailed description wherein a number of example embodiments and implementations are described and illustrated, including the best mode contemplated for carrying out the invention. The invention may also include other and different embodiments, and its several details may be modified in various respects, all without departing from the scope of the invention. Accordingly, the drawings and descriptions are to be regarded as illustrative in nature, and not as restrictive. The invention covers all modifications, equivalents, and alternatives falling within the scope of the invention.

BRIEF DESCRIPTION OF DRAWINGS

The skilled artisan will understand that the drawings, described below, are for illustration purposes only. The drawings are not necessarily drawn to scale and are not intended to limit the scope of this disclosure in any way.

FIGS. 1A, 1B, and 1C illustrate simplified schematic, front, and side views of an example battery-powered biosensor meter according to the prior art.

DESCRIPTION

Figure 2A:
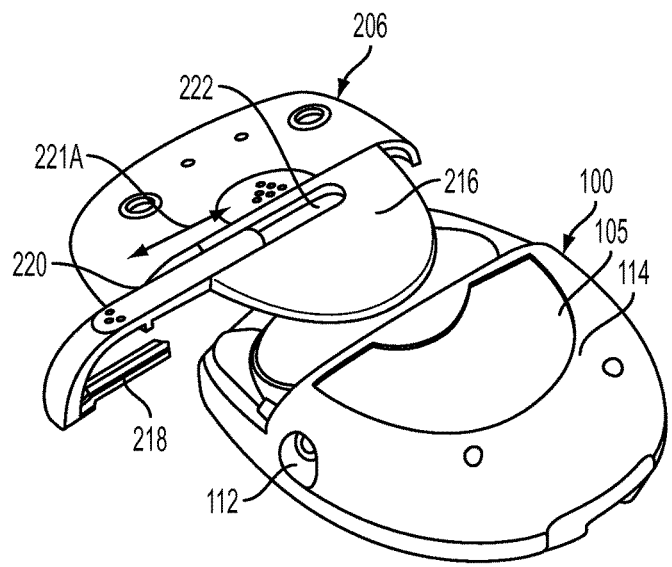
FIGS. 2A, 2B, and 2C illustrate a sequence of perspective views of a wireless transmitter adapter being attached to a biosensor meter according to embodiments.
Figure 2B:
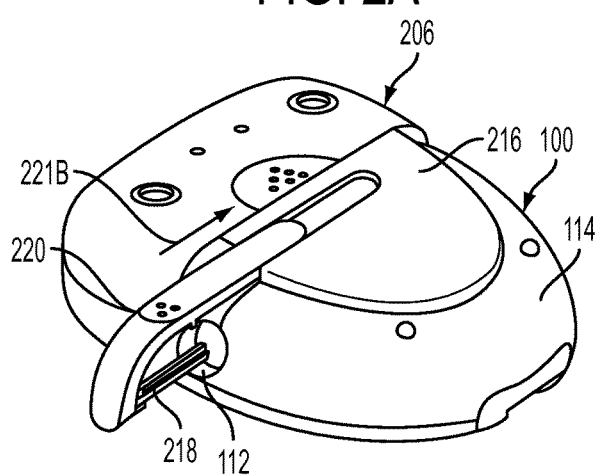

Reference will now be made in detail to the example embodiments of this disclosure, which are illustrated in the accompanying drawings. Wherever possible, the same reference numbers will be used throughout the drawings to refer to the same or like parts.

In one aspect, a wireless transmitter adapter can provide wireless communication capability to a battery-operated biosensor meter. The biosensor meter, which can be, e.g., a blood glucose meter, can be originally configured to download measurement data to a computer or like device via a hardwired cable connection. The wireless transmitter adapter can be configured, in some embodiments, to replace a battery cover of a biosensor meter. In other embodiments, the wireless transmitter adapter can be configured to surround most of the biosensor meter. The shape of the wireless transmitter adapter can conform to the shape of the biosensor meter such that no parts of the adapter protrude or dangle from the meter. This can avoid possible loss or damage of adapter parts and/or can avoid adversely affecting the convenience, handling, and/or use of the meter. In some embodiments, the wireless transmitter adapter can be powered by one or more batteries of the biosensor meter. In other embodiments, the wireless transmitter adapter can be powered by a separate power source carried in the wireless transmitter adapter. In some embodiments, the wireless transmitter circuitry can be configured to wirelessly upload and download data to and from the biosensor meter. The wireless transmitter adapter can allow a user to continue using an existing biosensor meter, while relieving the user of having to keep track of an appropriate data transfer cable and of having to manually connect the cable to a computer or like device each time data needs to be downloaded. In other aspects, methods of providing a wireless transmitter adapter for biosensor meters originally configured for hardwired data downloads are provided, as will be explained in greater detail below in connection with FIGS. 1-10.

FIGS. 1A-1C illustrate an example battery-powered biosensor meter 100, which can be, e.g., a blood glucose meter, according to the prior art. Biosensor meter 100 can be powered by first and second batteries 102a and 102b coupled in parallel and seated in a battery holder 103. First and second batteries 102a and 102b can each be, e.g., a coin or lithium cell type battery, such as, e.g., a 3-volt CR2032 battery. Battery holder 103 can be located in a battery compartment 104, which can be accessed from the back 105 of biosensor meter 100 via a removable battery cover 106. Biosensor meter 100 can also include circuitry that can include a microcontroller 107 and a memory 108 powered by first and second batteries 102a and 102b. Microcontroller 107 can be configured to determine a property of an analyte in a fluid, such as, e.g., a concentration of blood glucose in a sample of blood, and memory 108 can be configured to store measurement results. Microcontroller 107 can be a conventional microcontroller, such as, e.g., a V850 microcontroller by Renesas Electronics America Inc., of Santa Clara, Calif., or other similar microcontroller.

Biosensor meter 100 can include a display 109 and user interface actuators 110a, 110b, and 110c located on the front 111 of biosensor meter 100. Display 109 can display test results, time and date, battery life, and/or other information. User interface actuators 110a, 110b, and 110c can be, e.g., buttons, soft keys, scroll wheels, and/or the like. The number, type, and configuration of user interface actuators 110a, 110b, and 110c can be different than those shown. User interface actuators 110a, 110b, and 110c can be used to, e.g., turn biosensor meter 100 on and off, enter information and/or settings, initiate an analyte measurement test, recall and view test results, and/or initiate a data download from biosensor meter 100 to a computer or like device. Data downloads from biosensor meter 100 can occur via a hardwired cable connection from a communications port 112 of biosensor meter 100 to the computer or like device. Communications port 112 can be electrically coupled to microcontroller 107, memory 108, and/or other circuitry and, in various embodiments, can be configured to receive, e.g., a stereo plug, an RS232 plug, a USB plug, or any suitable electrical connector component.

Biosensor meter 100 can also include a test-sensor port 113. A user can insert a test strip into test-sensor port 113, apply a drop of a fluid sample (e.g., blood) to the test strip, and biosensor meter 100 can respond by analyzing the sample to determine, e.g., the blood glucose level in the sample.

Biosensor meter 100 can further include a housing 114 configured to house first and second batteries 102a and 102b, battery holder 103, battery compartment 104, microcontroller 107, memory 108, display 109, user interface actuators 110a, 110b, and 110c, communications port 112, test-sensor port 113, and any other components (not shown) of biosensor meter 100. Battery cover 106 can be removably attachable to housing 114 in any known manner. Biosensor meter 100 can be shaped differently than shown. An example of biosensor meter 100 can be the CONTOUR® USB Blood Glucose Meter by Bayer Healthcare, of Tarrytown, N.Y.

FIGS. 2A-C and FIGS. 3A and 3B illustrate a wireless transmitter adapter 206 configured for biosensor meter 100 and like biosensor meters in accordance with one or more embodiments. Wireless transmitter adapter 206 can have a body 216 configured to be disposed about and conform to at least a portion of biosensor meter 100. That is, body 216 can be configured to conform to the shape of at least a portion of biosensor meter 100 such that no parts of wireless transmitter adapter 206 protrude or dangle from biosensor meter 100. In some embodiments, body 216 can be configured to replace battery cover 106 of biosensor meter 100, as shown. Body 216 can attach to biosensor meter 100 in any suitable manner (e.g., with snap-in teeth that engage corresponding grooves or slots in housing 114 of biosensor meter 100). Body 216 can attach to biosensor meter 100 identically or similarly as battery cover 106. Body 216 can be molded and/or fabricated using any suitable techniques, and can be made from any suitable materials, including, e.g., suitable thermoplastic and/or elastomeric materials, such as ABS (acrylonitrile butadiene styrene), silicone, and TPE (thermoplastic elastomer) for flexible parts.

Figure 2C:
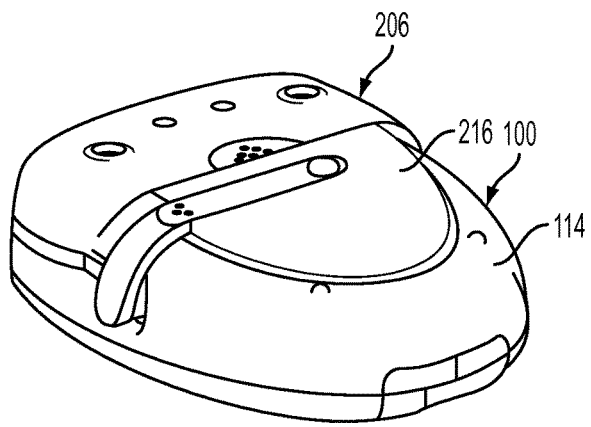
Figure 3A:
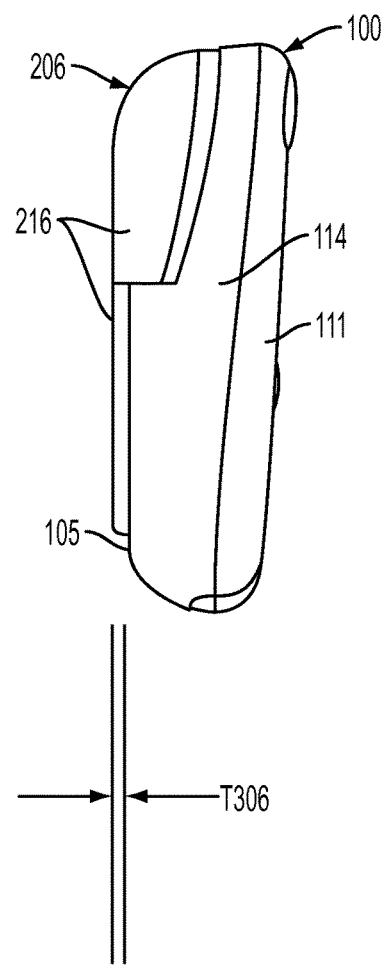
FIGS. 3A and 3B illustrate side and bottom views of a biosensor meter having a wireless transmitter adapter attached thereto according to embodiments.
Figure 3B:
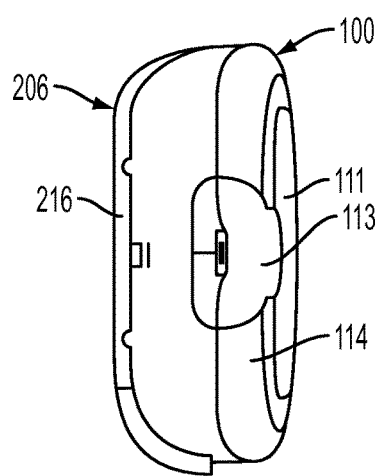

Wireless transmitter adapter 206 can include a connector 218 configured to be received in communications port 112 of biosensor meter 100 to electrically couple to circuitry (e.g., microcontroller 107) in biosensor meter 100 via communications port 112. Connector 218 can be mechanically and electrically compatible with communications port 112 and can include, e.g., a stereo plug, an RS232 plug, a USB plug, or any suitable electrical connector component that can electrically couple to circuitry in biosensor meter 100 via communications port 112. In some embodiments, connector 218 can include a slidable arm 220 that can extend or slide inward and outward (as indicated by arrow 221A) from body 216 along a corresponding groove 222 in body 216. To attach wireless transmitter adapter 206 to biosensor meter 100 and insert connector 218 into communications port 112, wireless transmitter adapter 206 and connector 218 can be positioned as shown in FIG. 2A. Body 216 can then be attached to housing 114 as described above and shown in FIG. 2B, wherein connector 218 is not yet received in communications port 112. Connector 218 can then be inserted into communications port 112 by pushing slidable arm 220 (as indicated by arrow 221B). FIGS. 2C, 3A, and 3B show wireless transmitter adapter 206 mechanically attached and electrically coupled to biosensor meter 100.

As best shown in FIGS. 3A and 3B, wireless transmitter adapter 206 can add a small thickness T306 to biosensor meter 100 when attached thereto. In some embodiments, body 216 of wireless transmitter adapter 206 can add a thickness T306 of only about 3 mm to back 105 of biosensor meter 100, thus not likely affecting the convenience, handling, and/or use of biosensor meter 100.

Figure 4:
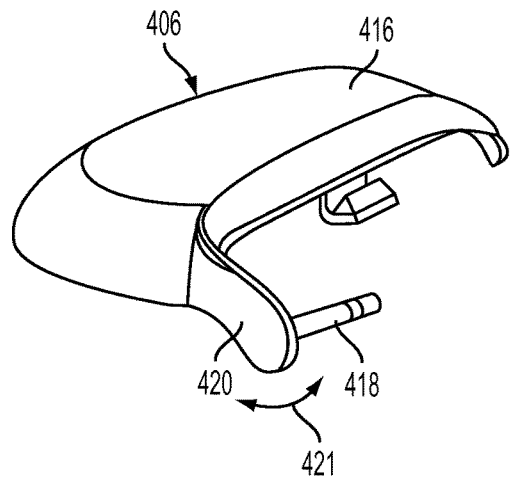
FIG. 4 illustrates a perspective view of a wireless transmitter adapter according to embodiments.
Figure 5:
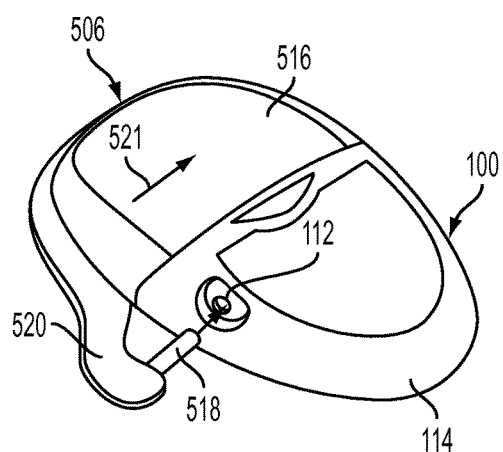
FIG. 5 illustrates a perspective view of another wireless transmitter adapter attached to a biosensor meter according to embodiments.
Figure 6:
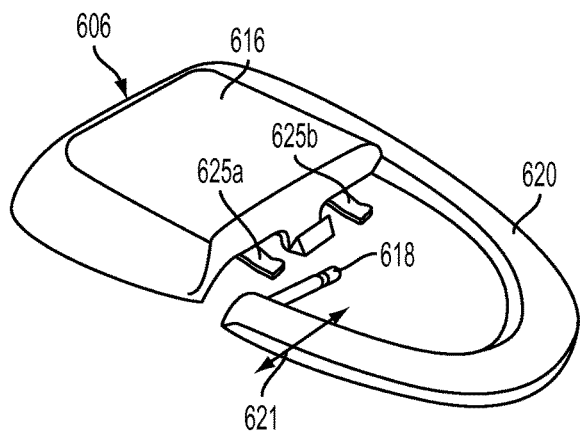
FIG. 6 illustrates a perspective view of still another wireless transmitter adapter according to embodiments.

FIGS. 4-6 illustrate alternative connectors that can be included in wireless transmitter adapter 206 in accordance with one or more embodiments. For example, FIG. 4 illustrates a wireless transmitter adapter 406 having a connector 418 that can include a flexible arm 420 extending from a body 416. Flexible arm 420 can be flexed as indicated by arrow 421 to allow connector 418 to be inserted into and removed from communications port 112. FIG. 5 illustrates a wireless transmitter adapter 506 having a connector 518 that can include a rigid arm 520. In this embodiment, a body 516 of wireless transmitter adapter 506 can attach to housing 114 of biosensor meter 100 by moving in a transverse direction indicated by arrow 521 such that as body 516 engages and attaches to housing 114, connector 518 is concurrently inserted into communications port 112. And FIG. 6 illustrates a wireless transmitter adapter 606 having a connector 618 that can include an elastomeric cord connector arm 620 extending from a body 616. Elastomeric cord connector arm 620 can be molded to conform to the shape of a bottom portion of biosensor meter 100 and can be flexed as indicated by arrow 621 to allow connector 618 to be inserted into and removed from communications port 112. Each of wireless transmitter adapters 406, 506, and 606 can be otherwise identical to wireless transmitter adapter 206, and each of connectors 418, 518, and 618 can be mechanically and electrically compatible with communications port 112 and can include, e.g., a stereo plug, an RS232 plug, a USB plug, or any suitable electrical connector component that can electrically couple to circuitry in biosensor meter 100 via communications port 112.

Figure 7:
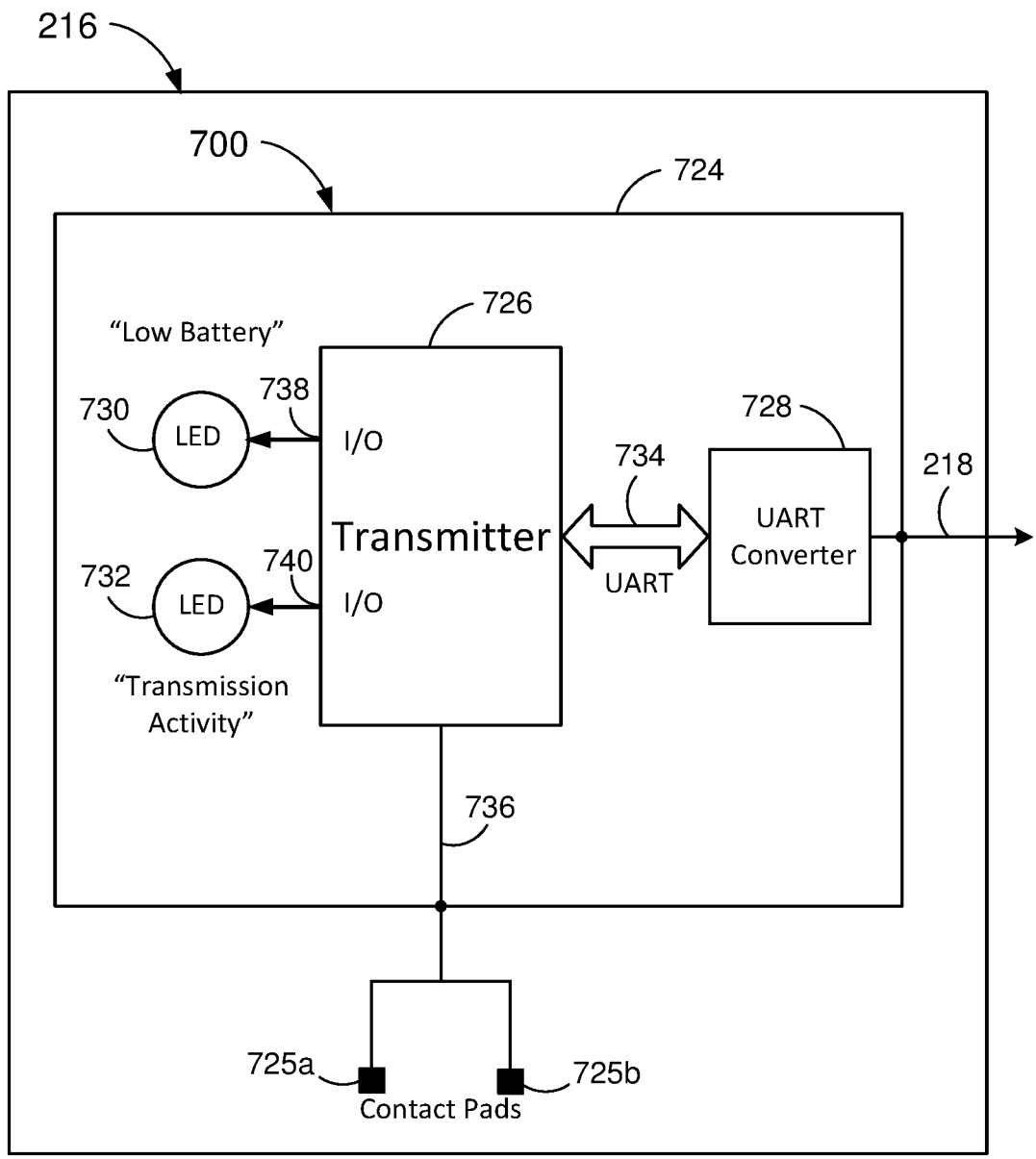
FIG. 7 illustrates a block circuit diagram of wireless transmitter circuitry of a wireless transmitter adapter according to embodiments.

FIG. 7 illustrates wireless transmitter circuitry 700 in accordance with one or more embodiments. Wireless transmitter adapter 206 can include wireless transmitter circuitry 700 housed within body 216. In some embodiments, wireless transmitter circuitry 700 can be an integrated circuit fabricated on a printed circuit board 724 or the like. Wireless transmitter circuitry 700 can be electrically coupled to connector 218 and can be configured to wirelessly transmit data from biosensor meter 100. In some embodiments, wireless transmitter circuitry 700 can include BLE (Bluetooth® low energy) wireless technology. In other embodiments, wireless transmitter circuitry 700 can be based on, e.g., RF (radio frequency), ZigBee®, or ANT wireless technologies. Alternatively, any suitable transmission technology can be used in wireless transmitter circuitry 700.

In some embodiments, wireless transmitter circuitry 700 can be powered by first and second batteries 102a and 102b of biosensor meter 100. That is, wireless transmitter adapter 206 does not have its own power source, but instead can be configured to draw power from the biosensor meter's power source. In some embodiments, wireless transmitter adapter 206 can include one or more electrical contacts 725a and 725b configured to electrically couple to one or more batteries of the biosensor meter to power wireless transmitter circuitry 700. Electrical contacts 725a and 725b can be positioned in body 216 such that respective electrical connections to first and second batteries 102a and 102b can be made upon attachment of body 216 to housing 114 of biosensor meter 100. For example, as shown in FIG. 6, wireless transmitter adapter 606 can include electrical contacts 625a and 625b positioned and mounted to body 616 such that attachment of body 616 to housing 114 of biosensor meter 100 electrically couples electrical contacts 625a and 625b to first and second batteries 102a and 102b, respectively.

In some embodiments, wireless transmitter circuitry 700 can include a transmitter 726, a UART (universal asynchronous receiver/transmitter) converter 728, a "Low Battery" LED 730 (light emitting diode), and a "Transmission Activity" LED 732. Wireless transmitter circuitry 700 can include other circuit components. UART converter 728, which can be, e.g., a UART-RS232 converter, can be electrically coupled to connector 218 and to a UART data bus 734, which is electrically coupled to transmitter 726. To receive power, transmitter 726 can be electrically coupled to electrical contacts 725a and 725b via at least one conductor 736. Transmitter 726 can also be electrically coupled to "Low Battery" LED 730 via an I/O (input/output) pin 738 and to "Transmission Activity" LED 732 via an I/O pin 740. In some embodiments, "Low Battery" LED 730 can be configured to illuminate or blink on and off when battery power received by transmitter 726 is below a predetermined amount. In some embodiments, "Transmission Activity" LED 732 can be configured to illuminate or blink on and off when wireless transmitter circuitry 700 is transmitting data.

In some embodiments, a user can wirelessly download data from biosensor meter 100 with wireless transmitter adapter 206 attached thereto in the same manner as hardwired data downloads from biosensor meter 100, except that a cable connection between biosensor meter 100 and a computer or like device is not needed. For example, a user in suitable proximity to a computer or like device may initiate a data download by selecting a data download function via display 109 and user interface actuators 110a, 110b, and 110c of biosensor meter 100. In some embodiments, no additional actions related to the wireless data transmission may be needed.

Figure 8A:
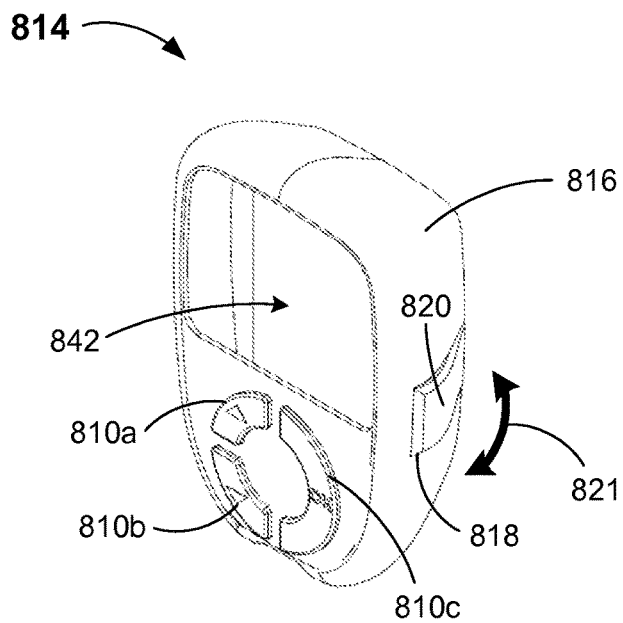
FIGS. 8A, 8B, and 8C illustrate a perspective top-front, a perspective bottom-front, and side views of a wireless transmitter adapter according to embodiments.
Figure 8B:
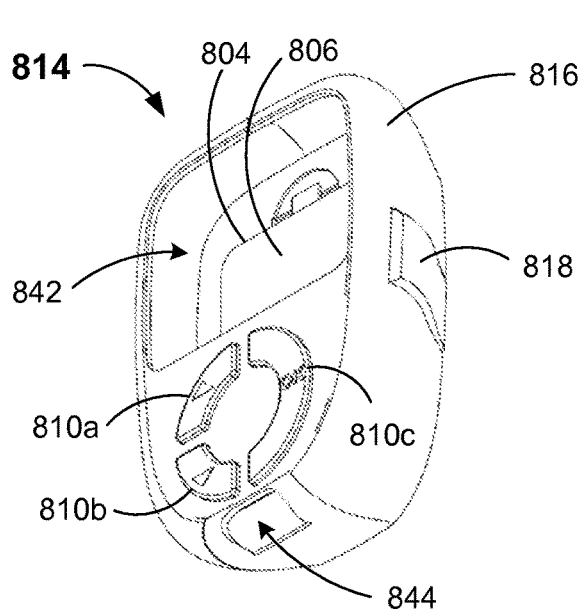
Figure 8C:
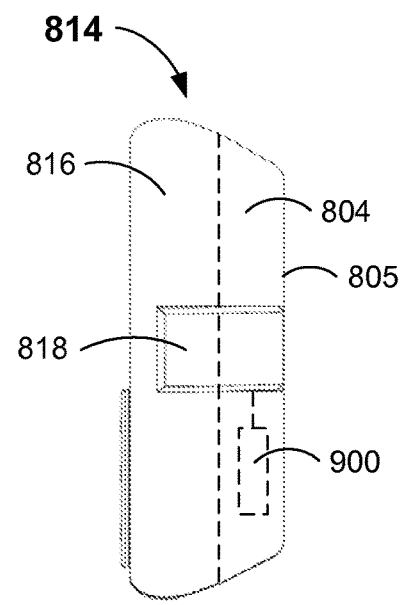

FIGS. 8A-C illustrate a wireless transmitter adapter 814 configured for biosensor meter 100 and like biosensor meters in accordance with one or more embodiments. Wireless transmitter adapter 814 can have a body 816 configured to be disposed about and conform to at least a portion of biosensor meter 100. That is, body 816 can be configured to conform to the shape of at least a portion of biosensor meter 100 such that no parts of wireless transmitter adapter 814 protrude or dangle from biosensor meter 100. In some embodiments, body 816 can be configured to surround at least a portion of biosensor meter 100. For example, as shown, body 816 can be configured to conform to and surround most of housing 114 of biosensor meter 100. Body 816 can have a front opening 842 sized and configured to allow biosensor meter 100 to slide into and out of body 816. Body 816 can be configured to allow stretching around front opening 842 to facilitate receiving and removing biosensor meter 100 therein and therefrom. Front opening 842 can be sized and positioned to allow display 109 of biosensor meter 100 to be viewed. Body 816 can have a bottom opening 844 sized and configured to provide access to test-sensor port 113 of biosensor meter 100. In some embodiments, body 816 can include raised areas 810a, 810b, and 810c sized and configured to cover and allow a user to actuate corresponding user interface actuators of biosensor meter 100. In some embodiments, body 816 can completely cover the top, back, and sides of biosensor meter 100, while covering a portion of the front and bottom of biosensor meter 100. Body 816 can be molded and/or fabricated using any suitable techniques, and can be made from any suitable materials, including, e.g., suitable thermoplastic and/or elastomeric materials, such as TPV (thermoplastic vulcanizate), TPU (thermoplastic polyurethane), IPE (thermoplastic elastomer), silicone elastomer, and silicone rubber. Also, different portions of body 816 can be made with different materials, thicknesses, or combinations thereof to have different characteristics (e.g., some portions can be made more rigid, while other portions can be made more flexible). In some embodiments, body 816 can be pre-shaped and have a modulus of elasticity that allows body 816 to conform closely to and snuggly fit over housing 114.

Wireless transmitter adapter 814 can include a connector 818 configured to be received in communications port 112 of biosensor meter 100 to electrically couple to circuitry (e.g., microcontroller 107) in biosensor meter 100 via communications port 112. Connector 818 (only partially shown in FIGS. 8A-C) can be mechanically and electrically compatible with communications port 112 and can include a suitable electrical connector plug (not shown) extending inside of body 816. Connector 818 can include, e.g., a stereo plug, an RS232 plug, a USB plug, or any suitable electrical connector component that can electrically couple to circuitry in biosensor meter 100 via communications port 112. In some embodiments, connector 818 can include a flexible arm 820 attached or hinged on one side of flexible arm 820 to body 816 that allows flexible arm 820 to flex outward (as indicated by arrow 821) from body 816. Accordingly, flexible arm 820 can be flexed outward prior to biosensor meter 100 being received in body 816, and then flexed inward toward communications port 112 to electrically couple connector 818 thereto.

Figure 9:
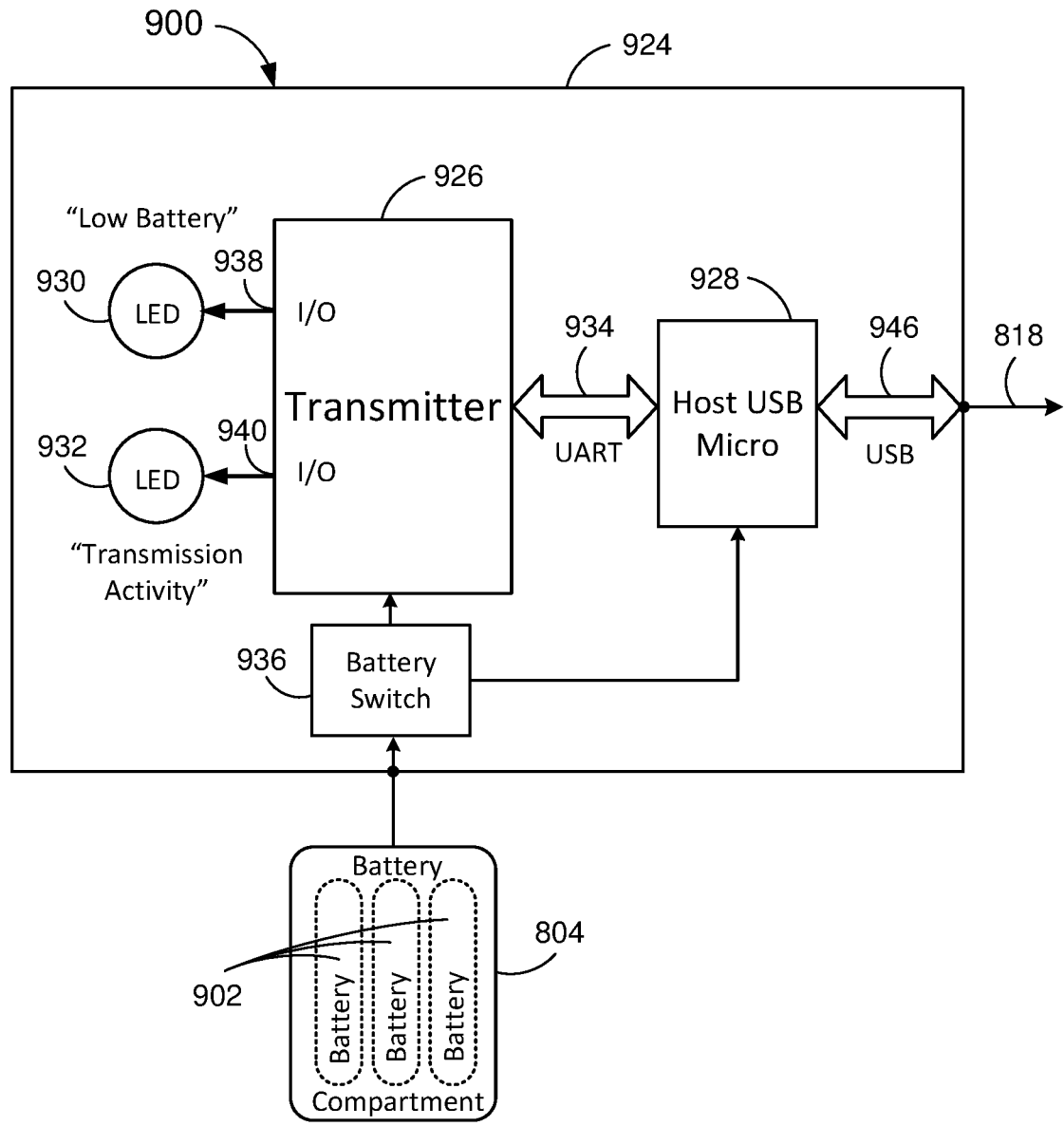
FIG. 9 illustrates a block circuit diagram of wireless transmitter circuitry of a wireless transmitter adapter according to embodiments.

FIG. 9 illustrates wireless transmitter circuitry 900 in accordance with one or more embodiments. Wireless transmitter adapter 814 can include wireless transmitter circuitry 900, which can be located within body 816 and can be electrically coupled to connector 818 to wirelessly transmit data from biosensor meter 100. In some embodiments, wireless transmitter circuitry 900 can be an integrated circuit fabricated on a printed circuit board 924 or the like. In some embodiments, wireless transmitter circuitry 700 can include BLE (Bluetooth® low energy) wireless technology. In other embodiments, wireless transmitter circuitry 900 can be based on, e.g., RF (radio frequency), ZigBee®, or ANT wireless technologies. Alternatively, any suitable transmission technology can be used in wireless transmitter circuitry 900.

In some embodiments, wireless transmitter circuitry 900 can be powered by a separate power source carried by wireless transmitter adapter 814. That is, wireless transmitter adapter 814 does not draw power from the biosensor meter's power source, but instead, body 816 can include a battery compartment 804 built there in, as shown in FIGS. 8B and 8C. Battery compartment 804 can be configured to hold one or more batteries 902 to power wireless transmitter circuitry 900. For example, in some embodiments, as shown in FIG. 9, wireless transmitter circuitry 900 can be powered by three AAA sized batteries 902. In some embodiments, battery compartment 804 can be accessed through front opening 842 via a removable battery cover 806 prior to biosensor meter 100 being received in body 816. In other embodiments, battery compartment 804 can be accessed from the back 805 of body 816.

In some embodiments, wireless transmitter circuitry 900 can include a transmitter 926, a host USB microcontroller 928, a "Low Battery" LED 930 (light emitting diode), a "Transmission Activity" LED 932, and a battery switch 936. Wireless transmitter circuitry 900 can include other circuit components. Transmitter 926 can be, in some embodiments, a BLE integrated circuit chip. USB microcontroller 928 can be electrically coupled to connector 818 via a USB data bus 946. USB microcontroller 928 can also be electrically coupled to transmitter 926 via a UART data bus 934. Transmitter 926 and USB microcontroller 928 can receive power via a battery switch 936 from one or more batteries 902 located in battery compartment 804. Transmitter 926 can also be electrically coupled to "Low Battery" LED 930 via an I/O (input/output) pin 938 and to "Transmission Activity" LED 932 via an I/O pin 940. In some embodiments, "Low Battery" LED 930 can be configured to illuminate or blink on and off when battery power received by transmitter 926 is below a predetermined amount. In some embodiments, "Transmission Activity" LED 932 can be configured to illuminate or blink on and off when wireless transmitter circuitry 900 is transmitting data.

With biosensor meter 100 received in and electrically coupled to wireless transmitter adapter 814, a user can, in some embodiments, wirelessly download data from biosensor meter 100 in the same manner as hardwired data downloads from biosensor meter 100, except that a cable connection from biosensor meter 100 to a computer or like device is no longer needed. For example, a user in suitable proximity to a computer or like device may initiate a data download by selecting a data download function via display 109 and user interface actuators corresponding to raised areas 810a, 810b, and 810c of wireless transmitter adapter 814. In some embodiments, no additional actions related to the wireless data transmission may be needed.

Figure 10:
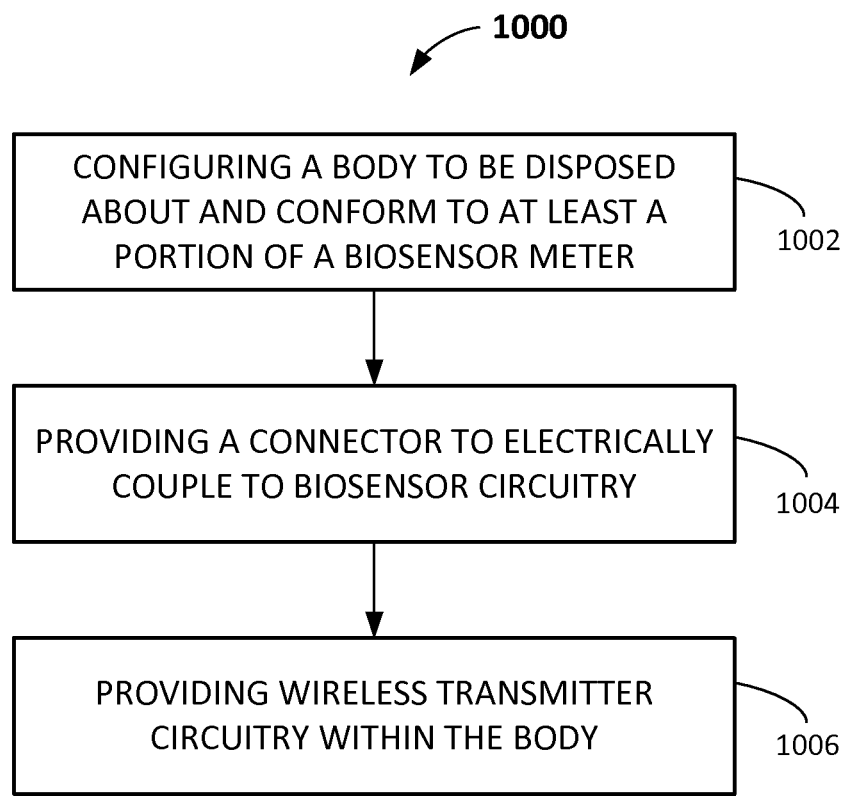
FIG. 10 illustrates a flowchart of a method of providing a wireless transmitter adapter configured for a biosensor meter capable of hardwired data downloads according to embodiments.

FIG. 10 illustrates a method 1000 of providing a wireless transmitter adapter configured for a biosensor meter capable of hardwired downloading of data in accordance with one or more embodiments. At process block 1002, method 1000 can include configuring a body of the wireless transmitter adapter to be disposed about and conform to at least a portion of a biosensor meter. In some embodiments, the body of the wireless transmitter adapter can be configured to replace a battery cover of the biosensor meter. For example, referring to FIGS. 2A-3B, the body of the wireless transmitter adapter can be body 216 of wireless transmitter adapter 206. In some embodiments, the body can be configured to conform to and surround most of the biosensor meter. For example, referring to FIGS. 8A-C, the body of the wireless transmitter adapter can be body 816 of wireless transmitter adapter 814, which can be configured to surround most of a biosensor meter.

At process block 1004, method 1000 can include providing a connector configured to be received in a communications port of the biosensor meter to electrically couple to circuitry in the biosensor meter via the communications port. In some embodiments, the connector can extend from the body of the wireless transmitter adapter and/or include one of an elastomeric cord connector arm, a rigid arm, a flexible arm, or a slidable arm. In some embodiments, the connector can include a stereo plug, an RS232 plug, a USB plug, or any suitable electrical connector component. For example, the connector can be connector 218, 418, 518, 618, or 818 of FIGS. 2A, 4, 5, 6, and 8A-C, respectively.

At process block 1006, method 1000 can include providing wireless transmitter circuitry within the body of the wireless transmitter adapter. The wireless transmitter circuitry can be electrically coupled to the connector and configured to wirelessly transmit data from the biosensor meter. In some embodiments, the wireless transmitter circuitry can be configured to be powered by one or more batteries of the biosensor meter via one or more electrical contacts built into the body of the wireless transmitter adapter. In other embodiments, the wireless transmitter circuitry can be powered by a separate power source (e.g., one or more batteries) installed in a battery compartment built into the body of the wireless transmitter adapter. The wireless transmitter circuitry can be, e.g., wireless transmitter circuitry 700 of FIG. 7 or wireless transmitter circuitry 900 of FIG. 9. Wireless data transmission via the wireless transmitter circuitry can be based on, e.g., ZigBee®, BLE (Bluetooth® low energy), or ANT wireless technologies. Alternatively, other suitable transmission technologies can be used.

The above process blocks of method 1000 can be executed or performed in an order or sequence not limited to the order and sequence shown and described. For example, in some embodiments, process block 1002 can be performed simultaneously with or after process blocks 1004 and/or 1006.

Persons skilled in the art should readily appreciate that the invention described herein is susceptible of broad utility and application. Many embodiments and adaptations of the invention other than those described herein, as well as many variations, modifications, and equivalent arrangements, will be apparent from, or reasonably suggested by, the invention and the foregoing description thereof, without departing from the substance or scope of the invention. For example, although described in connection with biosensor meters, one or more embodiments of the invention may be used with other types of battery-operated devices that are originally configured for hardwired data downloads. Accordingly, while the invention has been described herein in detail in relation to specific embodiments, it should be understood that this disclosure is only illustrative and presents examples of the invention and is made merely for purposes of providing a full and enabling disclosure of the invention. This disclosure is not intended to limit the invention to the particular apparatus, devices, assemblies, systems or methods disclosed, but, to the contrary, the intention is to cover all modifications, equivalents, and alternatives falling within the scope of the invention.

What is claimed is:

1. A biosensor meter, comprising:
    a battery holder configured to receive one or more batteries;
    a microcontroller configured to be powered by the one or more batteries and to determine a property of an analyte in a fluid;
    a memory configured to be powered by the one or more batteries and coupled to the microcontroller to store data including the determined property of the analyte in the fluid:
    a housing configured to house the battery holder, the microcontroller, and the memory;
    an externally accessible cable communications port disposed in and on the housing and configured to electrically couple a cable received in the cable communications port to the microcontroller; and
    a wireless transmitter adapter comprising:
        a body disposed about at least a portion of the housing, the body not disposed about the externally accessible cable communications port;
        a connector configured to be received in the externally accessible cable communications port to electrically couple to the microcontroller; and
        wireless transmitter circuitry located within the body and electrically coupled to the connector to wirelessly transmit the data from the biosensor meter, wherein the biosensor meter is a separately operable meter including a user interface configured to be usable without any part of the wireless transmitter adapter;
    wherein the body is configured to conform to and surround most of the housing.

2. The biosensor meter of claim 1, wherein the wireless transmitter circuitry is configured to be powered by the one or more batteries.

3. The biosensor meter of claim 1, wherein the body is configured to replace a battery cover of the biosensor meter.

4. The biosensor meter of claim 1, wherein the biosensor meter comprises a blood glucose meter and the data includes blood glucose measurement readings.

5. A method of providing a wireless transmitter adapter configured for a biosensor meter capable of hardwired downloading of data, the method comprising:
    configuring a body of the wireless transmitter adapter to be disposed about at least a portion of the biosensor meter, wherein the biosensor meter is a separately operable meter including a user interface configured to be usable without any part of the wireless transmitter adapter;
    providing a connector extending from the body and configured to be received in an externally accessible cable communications port of the biosensor meter to electrically couple to circuitry of the biosensor meter via the cable communications port, the body not configured to be disposed about the externally accessible cable communications port; and
    providing wireless transmitter circuitry within the body, the wireless transmitter circuitry electrically coupled to the connector and configured to wirelessly transmit the data from the biosensor meter;
    wherein the configuring the body comprises configuring the body to conform to and surround most of the biosensor meter.

6. The method of claim 5, wherein the configuring the body comprises configuring the body to replace a battery cover of the biosensor meter.

7. The method of claim 6 further comprising providing one or more electrical contacts configured to electrically couple to one or more batteries of the biosensor meter.

8. The method of claim 7, further comprising:
    replacing the battery cover of the biosensor meter with the body of the wireless transmitter adapter such that the one or more electrical contacts electrically couple to the one or more batteries to provide power to the wireless transmitter circuitry; and
    inserting the connector in the cable communications port to electrically couple to the circuitry of the biosensor meter.

9. The method of claim 5, wherein the biosensor meter comprises a blood glucose meter and the data comprises blood glucose measurement readings.

* * * * *